United States Patent [19]

Ku et al.

[11] Patent Number: 5,034,412
[45] Date of Patent: Jul. 23, 1991

[54] METHOD OF INHIBITING INTERLEUKIN-1 RELEASE

[75] Inventors: George Ku, Cincinnati; Niall Doherty, West Chester, both of Ohio

[73] Assignee: Merrell Dow Pharmacueticals Inc., Cincinnati, Ohio

[21] Appl. No.: 629,798

[22] Filed: Dec. 19, 1990

Related U.S. Application Data

[60] Division of Ser. No. 387,328, Jul. 28, 1989, which is a division of Ser. No. 151,521, Feb. 18, 1988, Pat. No. 4,870,101, which is a continuation-in-part of Ser. No. 26,587, Mar. 17, 1987, abandoned.

[51] Int. Cl.$^5$ ..................... A01N 37/00; A01N 47/10; A01N 31/00
[52] U.S. Cl. .................................. 514/529; 514/476; 514/730; 514/824; 514/863; 514/866; 514/886

[58] Field of Search ........................................ 514/529

[56] References Cited

PUBLICATIONS

Chemical Abstracts, vol. 110 (14) 121449b.

*Primary Examiner*—Stanley S. Friedman
*Assistant Examiner*—T. J. Criares
*Attorney, Agent, or Firm*—Louis J. Wille

[57] ABSTRACT

Methods useful for inhibiting the release of interleukin-1 and for alleviating interleukin-1 mediated conditions, such as IL-1-mediated inflammation, comprising administration of an effective amount of a pharmaceutically acceptable antioxidant compound such as disulfiram, tetrakis [3-(2,6-di-tert-butyl-4-hydroxyphenyl)propionyloxy methyl]methane or 2,4-di-isobutyl-6-(N,N-dimethylaminomethyl)-phenol.

5 Claims, No Drawings

METHOD OF INHIBITING INTERLEUKIN-1 RELEASE

CROSS-REFERENCE TO RELATED APPLICATION

This is a divisional of application Ser. No. 387,328, filed July 28, 1989, which is a divisional of application Ser. No. 151,521, filed Feb. 18, 1988, now U.S. Pat. No. 4,870,101, issued on Sept. 26, 1989, which is a continuation-in-part of Ser. No. 026,587, filed Mar. 17, 1989, now abandoned.

BACKGROUND OF THE INVENTION

Field of the Invention

Interleukin-1 (IL-1) is the name for a family of molecules which have multiple biological effects. The name interleukin-1 was proposed in 1979; and earlier literature reports refer to it by some other name. Murphy, *British Journal of Rheumatology*, 1985; 24(suppl 1): 6-9, and Oppenheim et al., *Immunology Today*, vol. 2, 45-55(1986). IL-1 is secreted by stimulated macrophages, and has several significant biological effects, such as mediation of T-lymphocyte proliferation and pyrogenic and proinflammatory effects.

IL-1 activities are summarized in the two above papers. IL-1 has been described to mediate the acute phase response in inflammation, and to have pyrogenic and proinflammatory effects. IL-1 induces connective tissue changes, and has been demonstrated to induce the release of degradative enzymes from mesenchymal cells that are present at the sites of bony erosion in inflammatory disease states, such as rheumatoid arthritis. Billingham, *Brit. J. Rheumatology*, 1985:24(suppl 1):25-28. Dayer, *Brit. J. Rheumatology*, 1985:24(suppl 1):15-20. The production of acute phase proteins in the hepatocytes during the acute phase of inflammation is mediated by IL-1. Whicher, *Brit. J. Rheumatology*, 1985:24(suppl 1):21-24.

IL-1 is also involved as a mediator in the infalmmatory skin disease, psoriasis. Camp et al., J. Immunology 1986: 137: 3469-3474, and Ristow, Proc. Natl. Acad. Sci. USA 1987: 84: 1940-1944. It is cytotoxic for insulin producing beta cells in the pancreas, and is thus a causative factor in the development of diabetes mellitus. Bendtzen et al., Science 1986: 232: 1545-1547 and Marx, Science 1988: 239: 257-258, . IL-1 also appears to be involved in the development of athersoclerotic lesions or athersclerotic plaque. Marx, Science 1988: 239: 257-258. In the absence or suppression of endogenous prostaglandins, IL-1 stimulates growth and proliferation of vascular smooth muscle cells, which could lead to thickening of vascular walls, such as occurs in atherogenesis. Libby et al., Fed. Proc. March 1, 1987: Vol. 46, no. 3: 975, Abstract 3837.

It would be advantageous to control the release of IL-1, and to be able to treat IL-1-mediated effects. It would also be advantageous to control or treat IL-1 mediated inflammations, without production of concomitant side effects known to accompany the use of antiinflammatory steroids and non-steroidal antiinflammatory agents.

SUMMARY OF THE INVENTION

It has now been found that certain pharmaceutically-acceptable compounds can be used to inhibit the the release of IL-1, and thus to control or treat IL-1 mediated conditions. Compounds useful in practicing the method of the invention include disulfiram, tetrakis [3-(2,6-di-tert-butyl-4-hydroxyphenyl) propionyloxy methyl] methane and 2,4-di-isobutyl-6-(N, N-dimethylaminomethyl)phenol. Although the compounds have diverse structures, the compounds all have antioxidant activity. Tetrakis [3-(2,6-di-tert-butyl-4-hydroxyphenyl) propionyloxy methyl] methane (also named as Irganox 1010 or as benzenepropanoic acid: 3,5-bis(1,1-dimethylethyl)-4-hydroxy-, tetraester with 2,2-bis(hydroxymethyl)1,3-propanediol) is commercially used as an anantioxidant. The causal mechanism of any relationship between antioxidant activity of the compounds and their ability to inhibit IL-1 release is not known, and the invention is not limited to any particular theoretical mechanism.

Such compounds can be administered to animals to inhibit secretion of IL-1; to inhibit or treat IL-1-mediated effects; and to inhibit or treat IL-1-mediated inflammation.

In the method of the invention, one or more compound is administered to an animal, typically to a mammal in need of inhibition of IL-1 secretion, inhibition of IL-1-mediated effects, or inhibition of IL-1-mediated inflammation, in an amount effective to produce such inhibition. The compounds can be administered to inhibit or treat IL-1-mediated effects in conditions such as inflammation, psoriasis, atherosclerosis, and diabetes.

The compounds can be administered by conventional routes, oral administration being preferred. The dosage to be employed will vary according to factors such as the species, age, weight and condition of the particular animal being treated, and the particular compound employed. Optimum dosages in particular situations can be determined by conventional dose range finding techniques.

In general, dosage levels for the use of the compounds to inhibit IL-1 release can be ascertained by conventional range finding studies. The compounds are preferably administered orally at daily dosages from about one to about 300 milligrams of active ingredient per kilogram of animal body weight. Useful results in inhibition of IL-1 release have been obtained with daily oral dosages of 100 milligrams per kilogram of animal body weight (mg/kg).

Although some of the compounds of the method of the invention, such as disulfiram, are known to produce pharmacologic effects unrelated to IL-1 release, they can be usefully employed in the method of the invention with animals which are not in need of such other pharmacologic action. In certain cases, the other pharmacologic action may be regarded as an undesirable side effect, when the desired result is inhibition of IL-1 release. Thus, with disulfiram, for example, concomitant administration of ethanol should be avoided, to avoid the well known reaction to alcohol.

The compounds used in the invention can be formulated in conventional pharmaceutically-acceptable carriers to provide unit dosage forms convenient for administration. In general, known dosage forms and carrier materials can be used.

The invention is further illustrated in the following Example.

EXAMPLE

Peritoneal macrophages obtained from CD-1 mice were collected and washed once with RPMI-1640 medium (GIBCO, Grand Island, N.Y.) containing 100 Units/ml penicillin, 100 µg/ml streptomycin and 25

μg/ml fungizone (GIBCO, Grand Island, N.Y.). Cells were suspended at $6 \times 10^6$ cells per ml, and one ml aliquots were plated into 6-well flat-bottom plates. After one hour incubation at 37° C. in a humidified air chamber containing 5% $CO_2$, nonadherent cells were removed and 1 ml RPMI medium (with or without lipopolysaccharide (LPS) - 100 μg/well) was added to each well; LPS stimulates macrophages to release IL-1. Incubation was continued for 6 hours, after which the culture supernatant was collected and filtered through 0.22 micrometer Acrodisc filters (Gelman, Ann Arbor, Mich.). The fluid was stored at a temperature of $-70°$ C. until assayed for IL-1 activity.

IL-1 activity was determined by the C3H/HeJ thymocyte proliferation assay of Mizel et al., J. Immunol. 120:1497 (1978). In this procedure, thymocytes of C3H/HeJ mice are incubated with the macrophage culture supernatant in the presence of phytohemagglutinin, and pulsed by incubation with $^3$H-thymidine. The cells are then harvested and radioactivity is determined by liquid scintillation counting. IL-1 activity was expressed as units defined according to Mizel et al, J. Immunol. 120:1497 (1978).

Compounds were tested in this procedure by oral administration to CD-1 mice 40, 24 and 16 hours prior to collection of peritoneal macrophages. The dosage used was 100 mg/kg. The compounds and results obtained are set out in the following table.

| Compound | Percent Reduction of IL-1 Secretion |
|---|---|
| Disulfiram | 79.0% |
| Tetrakis [3-(2,6-di-tert-butyl-4-hydroxyphenyl)propionyloxy methyl] methane | 66.8% |
| 2,4-Di-isobutyl-6-(N, N-dimethylaminomethyl)-phenol | 92.5% |

The above results indicate significant inhibition of IL-1 release was obtained with the test compounds.

What is claimed is:

1. A method of inhibiting the release of interleukin-1 in animals which comprises administering to an animal in need thereof an amount of tetrakis (3-(2,6-di-tert-butyl-4-hydroxyphenyl)propionyloxy methyl)methane effective in inhibiting the release of interleukin-1.

2. Method of claim 1 wherein the animal is suffering from inflammation and the compound is administered in an amount sufficient to alleviate the inflammation.

3. Method of claim 1 wherein the animal is suffering from psoriasis and the compound is administered in an amount sufficient to alleviate the psoriasis.

4. Method of claim 1 wherein the animal is suffering from diabetes and the compound is administered in an amount sufficient to alleviate the diabetes.

5. Method of claim 1 wherein the animal is suffering from atherosclerosis and the compound is administered in an amount sufficient to alleviate the atherosclerosis.

* * * * *